United States Patent [19]

Dickerson et al.

[11] Patent Number: 4,675,108

[45] Date of Patent: Jun. 23, 1987

[54] APPARATUS FOR TREATING WASH WATER FROM THE MANUFACTURE OF TEREPHTHALIC ACID

[75] Inventors: Richard C. Dickerson; William S. Miller, both of Virginia Beach, Va.

[73] Assignee: Ecolochem, Inc., Norfolk, Va.

[21] Appl. No.: 748,755

[22] Filed: Jun. 26, 1985

Related U.S. Application Data

[62] Division of Ser. No. 556,338, Nov. 30, 1983, Pat. No. 4,540,493.

[51] Int. Cl.$^4$ ............................................. B01J 47/02
[52] U.S. Cl. .................................... 210/275; 210/269; 210/284
[58] Field of Search ............... 210/669, 670, 678, 685, 210/269, 275, 284

[56] References Cited

U.S. PATENT DOCUMENTS

| | | | |
|---|---|---|---|
| 2,572,575 | 10/1951 | Shafer et al. | 260/525 |
| 2,572,710 | 10/1951 | Emerson et al. | 260/525 |
| 2,822,388 | 2/1958 | Horn et al. | 260/525 |
| 2,829,160 | 4/1958 | Stehman et al. | 260/525 |
| 2,846,468 | 8/1958 | York | 260/525 |
| 2,862,963 | 12/1958 | Fuchs et al. | 260/525 |
| 3,171,856 | 3/1965 | Kurtz | 260/525 |
| 3,205,260 | 9/1965 | Costabello | 260/525 |
| 3,243,456 | 3/1966 | Caldwell et al. | 260/525 |
| 3,334,044 | 8/1967 | Satterlee | 210/685 |
| 3,592,847 | 7/1971 | Gallivan et al. | 260/525 |
| 3,680,701 | 8/1972 | Holca | 210/284 |
| 3,746,754 | 7/1973 | Cines | 260/524 R |
| 3,770,819 | 11/1973 | Norton | 260/515 P |
| 3,850,983 | 11/1974 | Park | 260/525 |
| 3,985,648 | 10/1976 | Casolo | 210/669 |
| 4,201,871 | 5/1980 | Tanouchi et al. | 562/486 |
| 4,212,991 | 7/1980 | Choulet et al. | 562/480 |
| 4,215,224 | 7/1980 | Wallace et al. | 562/485 |
| 4,340,752 | 7/1982 | List et al. | 562/485 |
| 4,357,475 | 11/1982 | Hanotier et al. | 562/414 |
| 4,383,920 | 5/1983 | Muller et al. | 210/284 |

Primary Examiner—Ivars Cintins
Attorney, Agent, or Firm—Lane & Aitken

[57] ABSTRACT

A process for treating wash water from the manufacture of terephthalic acid, wherein the wash water includes terephthalic acid, metal catalyst, and organic acid byproducts. The process includes the steps of passing the wash water through a filter medium to remove undissolved terephthalic acid solids, passing the filtered water through a cation exchange resin in hydrogen ion form to remove the metal catalysts, and passing the water through an anion exchange resin to remove dissolved terephthalic acid and dissolved organic acid byproducts. The treated water and certain components removed from the wash water are recovered and reused in the manufacture of additional terephthalic acid. An apparatus in which the process is practiced is also described and, after a quantity of wash water has been treated, the apparatus is regenerated with regenerants that are also recovered and reused in the manufacture of additional terephthalic acid.

5 Claims, 2 Drawing Figures

APPARATUS FOR TREATING WASH WATER FROM THE MANUFACTURE OF TEREPHTHALIC ACID

This is a division of application Ser. No. 556,338 filed Nov. 30, 1983, now U.S. Pat. No. 4,540,493 issued Sept. 10, 1985.

1. FIELD OF THE INVENTION

This invention pertains to the recovery and recycling of organic acids, water and other valuable wash water constituents produced in the manufacture of terephthalic acid.

2. BACKGROUND OF THE INVENTION

Technical-grade terephthalic acid is produced primarily by the liquid-phase air oxidation of p-xylene. In a typical process, an oxidation reactor is provided and solvent, air, p-xylene and catalyst are continuously fed into the reactor where oxidation takes place at elevated temperatures. Acetic acid can be used as the solvent, one or more multivalent metals, such as cobalt and manganese, can be used as the catalyst, and bromine can be used as a renewable source of free radicals. The terephthalic acid leaves the reactor in the form of a slurry and, after passing the slurry through a surge vessel which operates at a lower temperature and pressure than the reactor, the acid is recovered by centrifuging, washing and drying the acid crystals. A typical terephthalic acid manufacturing process involving liquid-phase air oxidation of p-xylene is depicted in Kirk-Othmer, *Encyclopedia of Chemical Technology*, Vol 17 (1982), on page 749. Other terephthalic manufacturing operations involve similar steps and reactants.

When the terephthalic acid crystals are washed, the wash water carries away uncrystallized terephthalic acid, unwanted byproducts such as p-toluic acid and benzoic acid, and catalysts from the terephthalic acid crystals. Terephthalic acid manufacturing plants generate large amounts of such wash water and environmental control standards prevent the discharging of the untreated water into natural waterways. In the past, the environmentally offensive components of the wash water have been removed by retaining the water in biological lagoons for extended periods of time, whereby microbial action reduces certain components to innocuous constituents. However, this treatment is expensive and time-consuming. Further, the biological lagoons do not always remove all of the components contained in the wash water, so that recycling of the water is not possible.

Importantly, previous treatments of the wash water have also failed to enable recovery and reuse of any components of the wash water. When the components are removed by treatment in biological lagoons, they are either destroyed by bacteria or deposited on the lagoon bottom in the form of unusable sludge.

Accordingly, there exists a need in the art for an improved process for treating wash water produced in the manufacture of terephthalic acid. The process should be capable of removing components from the wash water, such that the water can be discharged into natural waterways or, preferably, recycled for reuse in the manufacture of additional terephthalic acid. Preferably, the process should enable the recovery of valuable components of the wash water, such that the components can be reused in the manufacture of additional terephthalic acid. In an especially preferred embodiment, the process should be practiced in an apparatus, the regeneration of which would be accomplished by regenerating substances that could also be recovered and reused in the acid manufacturing process. The process should be efficient and economical and thus would advantageously eliminate the need for large areas presently required for prior art biological lagoons. These objectives are satisfied by the present invention. Other objectives of the invention will become apparent from the following.

SUMMARY OF THE INVENTION

The present invention is a process for treating wash water from the manufacture of terephthalic acid, wherein the wash water includes terephthalic acid, metal catalyst, and organic acid byproducts. The process includes the steps of passing the wash water through a filter medium to remove undissolved acid solids, passing the filtered water through a cation exchange resin in hydrogen ion form to remove the metal catalysts, and passing the water through an anion exchange resin to remove dissolved terephthalic acid and dissolved organic acid byproducts. The treated water and certain components removed from the wash water are recovered and reused in the manufacture of additional terephthalic acid. An apparatus in which the process is practiced is also described and, after a quantity of wash water has been treated, the apparatus is regenerated with regenerants that are also recovered and reused in the manufacture of additional terephthalic acid.

DESCRIPTION OF THE PREFERRED EMBODIMENTS

Figure 1:
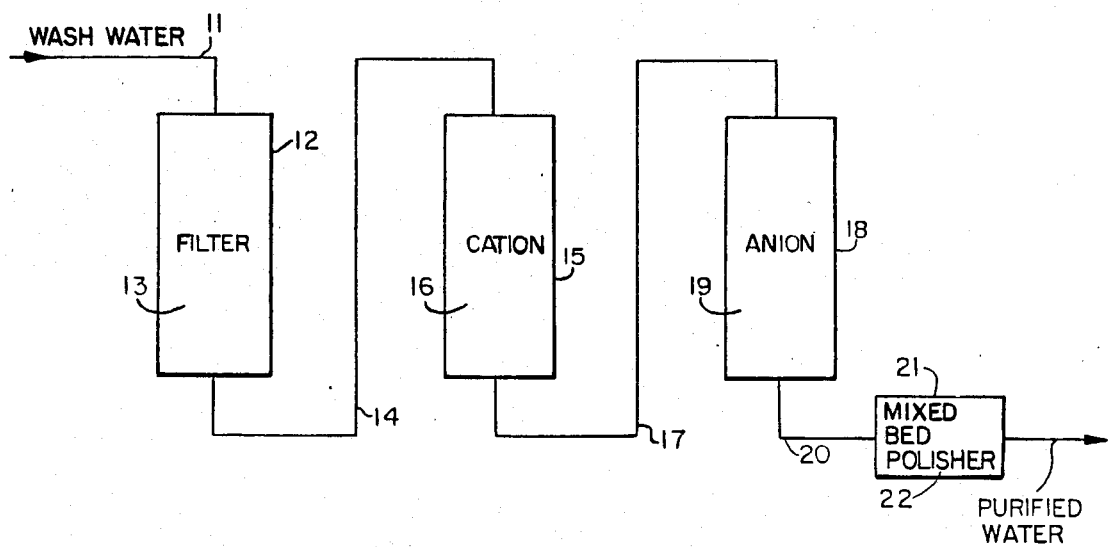
FIG. 1 is a flow chart depicting the apparatus and process steps of the present invention in a service cycle.
Figure 2:
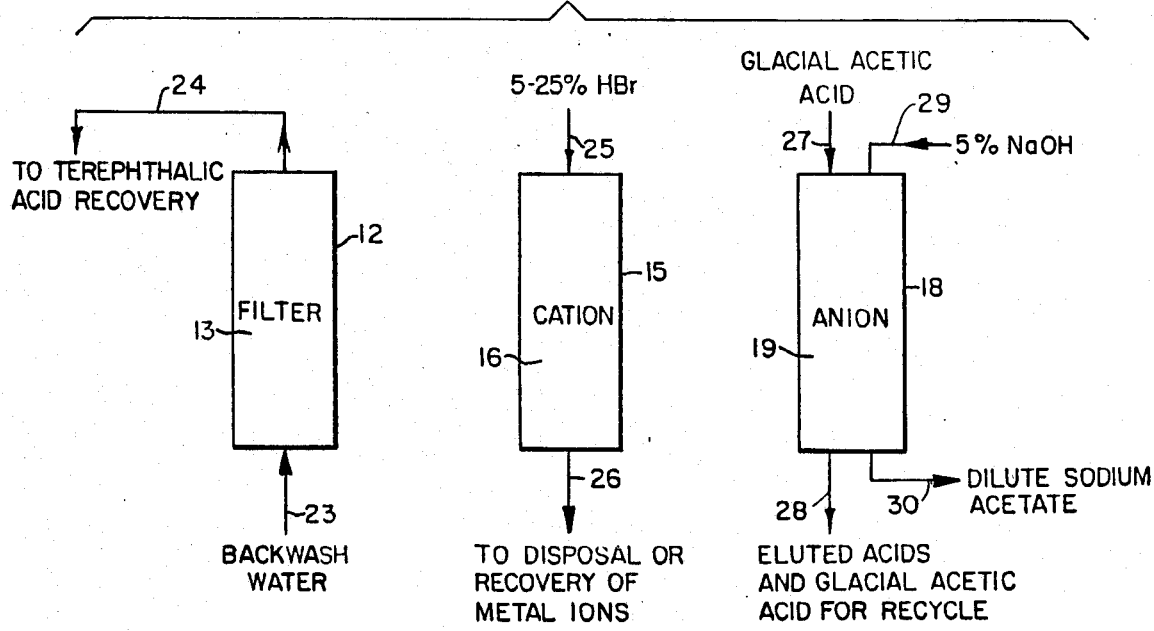
FIG. 2 is a flow chart depicting the apparatus and process steps of the present invention in a regeneration cycle.

In accordance with the present invention, an apparatus for treating wash water from a terephthalic acid manufacturing process is schematically illustrated in FIGS. 1 and 2. In FIG. 1, a service cycle is depicted and, in FIG. 2, a regeneration cycle is depicted. The wash water is derived from the wash cycle of a terephthalic acid manufacturing operation, whereby uncrystallized terephthalic acid, metal catalysts, and unwanted organic acid byproducts have been carried away from terephthalic acid crystals. The process is advantageously used to treat wash water from the terephthalic acid manufacturing operation described above, but wash water from any terephthalic acid manufacturing operation is also advantageously treated when the water contains organic acids and catalysts similar to those described herein. The metal catalysts are used in the prior art to catalyze the oxidation reaction in the formation of terephthalic acid, and include multivalent metals such as cobalt and manganese. The organic acid byproducts include p-toluic acid, benzoic acid and other organic acid byproducts.

Wash water from a terephthalic acid manufacturing operation can initially have an elevated temperature of about 300° F. As will be discussed more fully hereinbelow, the apparatus in which the water is treated comprises ion exchange resins, and a temperature of 300° F.

can damage the resins and reduce their capacity. Accordingly, the wash water is cooled to a temperature at which the resins will not be damaged before introducing the water into the apparatus. A temperature of up to about 140° F. is sufficient for presently available resins, but could be higher for resins that can sustain higher temperatures without damage. On the other hand, cold temperatures can inhibit the flow of water through the system, so that the water is preferably not cooled below about 32° F. before being introduced into the apparatus.

The wash water is passed through a conduit 11 and filter 12, as depicted in FIG. 1. A filter medium 13 is selected that will cause any undissolved acid solids in the wash water to be deposited thereon. Suitable filter media include filter sand, anthracite and garnet, and a granule diameter is selected that will cause the deposition of undissolved acid solids. A suitable filter medium is sand having a granule diameter of from 0.3 to 1.0 mm. In a preferred embodiment, filter sand having a granule diameter of 0.45 mm, or about a 40 mesh, is used.

Following filtration, the wash water is passed through a conduit 14 and cation bed 15. The bed contains a cation resin 16, in hydrogen ion form, which functions to remove any catalysts, such as cobalt and manganese, that might otherwise foul the downstream anion resin. Any commercially available strong or weak acid cation resin can be used, a strong acid resin being preferred. Ionac C-250, a strong acid cation resin in hydrogen ion form, manufactured by the Sybron Corporation, Birmingham, N.J., is employed in a preferred embodiment.

After the metal catalysts are removed from the wash water, it is passed through conduit 17 to anion bed 18. The anion exchange resin 19 contained in the bed removes substantially all dissolved organic acid by-products, including p-toluic acid and benzoic acid, as well as any terephthalic acid that was not removed by filter medium 13. For this purpose, any commercially available strong, weak or intermediate base anion exchange resin is suitable, a weak or intermediate base anion resin being preferred. An example of a preferred anion resin is Ionac-365, an intermediate base anion resin manufactured by Sybron Corporation. By removing the metal catalysts before passing the wash water through the anion exchange resin, the possibility of fouling the anion resin is reduced. In an alternative but less preferred embodiment, the filtration step is eliminated and undissolved acid solids are recovered on the cation exchange resin, but the cation resin capacity may be reduced in this case due to fouling by undissolved acid After the organic acids have been removed, an optional step consists of passing the wash water through conduit 20 and polisher 21, which contains mixed-bed resins 22. The mixed-bed resins can consist of any commercially available strong acid cation exchange resin and strong base anion exchange resin. In a preferred embodiment, Ionac C-249 is used as the cation resin and Ionac ASB-1 is used as the anion resin.

The wash water treated in the above-described service cycle is capable of being suitable for discharge into waterways without violating present environmental standards. More advantageously, the water is recycled for reuse in washing additional terephthalic acid in the terephthalic acid manufacturing process Thus, the present invention eliminates the need for biological lagoons and treated wash water can be recycled over and over again. Costs are saved not only by eliminating the disposal problems of the prior art, but also by reducing or eliminating the costs of supplying wash water of a suitable purity.

After a quantity of wash water has been treated, a regeneration cycle is instituted to regenerate the filter medium and ion exchange resins, and to recover the valuable components removed from the water. This regeneration cycle is depicted in FIG. 2.

During the regeneration cycle, filter medium 13 is backwashed by passing backwash water through conduit 23, filter 12, and conduit 24, such that the flow through the filter medium is opposite to the flow during the service cycle. By backwashing, undissolved acid solids collected by the filter medium are removed from the filter, and the solids are recovered from the backwash water by decantation. In this fashion, terephthalic acid that is typically lost in a waste stream in prior art processes is added to the overall product yield of the manufacturing process. After the decantation step, the backwash water can be disposed of or, preferably, recycled.

Regeneration of the cation exchange resin involves the removal of the metal catalysts from the resin. This can be accomplished by contacting the resin with any acid that is capable of displacing the metal ions from the resin without damaging the resin. A regenerating acid selected from the group consisting of any strong mineral acid, such as hydrobromic or hydrochloric acid is suitable. Hydrobromic acid diluted to 2 to 48% is suitable and hydrobromic acid diluted to 5 to 25% is especially preferred because it is very effective in the regeneration of the cation resin and, at the same time, can be recycled into certain terephthalic acid manufacturing operations. After being used in one regeneration cycle, the hydrobromic acid is directly recycled to the terephthalic acid manufacturing operation or is first reused in subsequent regeneration cycles before such recycling. Regeneration is effected by passing the regenerating acid through conduit 25, cation resin 16, and conduit 26. During the regeneration step, the cation resin releases the metal catalysts and these can be disposed of or, preferably, also recycled in the manufacture of additional terephthalic acid.

Regeneration of the anion exchange resin involves the removal of the terephthalic acid and byproducts from the resin. This can be accomplished by first passing any weak acid that is capable of displacing the terephthalic acid and byproducts, without damaging the resin, through conduit 27, anion resin 19, and conduit 28. Glacial acetic acid and formic acid are suitable for this purpose, the former being preferred because it is recyclable in manufacturing operations that employ acetic acid as a solvent in the air oxidation of p-xylene to form terephthalic acid. The weak acid elutes any dissolved p-toluic acid, benzoic acid, and terephthalic acid that was deposited on the anion resin during the service cycle. Second, any alkali that is capable of displacing the weak acid from the resin without damaging the resin, such as ammonia, sodium carbonate, potassium hydroxide or sodium hydroxide, is passed through conduit 29, anion resin 19, and conduit 30 to remove any weak acid trapped by the resin. In a preferred embodiment, sodium hydroxide, diluted to 5 to 10%, is used and the resultant effluent, which consists of sodium acetate and any exces sodium hydroxide, is disposed of or processed for reuse. In one embodiment, the effluent is reused in subsequent regeneration cycles to remove additional weak acid.

Following the regeneration cycle, the apparatus is once again ready to treat additional wash water.

The apparatus comprises resin and filter tanks, valves, conduits and appropriate accessory equipment that is adapted to receive the appropriate resins and filter media of the present invention. Such a system is described in U. S. Pat. No. 4,383,920, which is hereby incorporated by reference. Modifications of such a system to meet the needs of the present invention can be made by one of ordinary skill in the art. In one particular, it will be apparent that the use of strong acids such as hydrobromic acid in certain of the tanks will suggest the inappropriateness of rubber lining in such tanks, and tanks having appropriate linings would be selected.

Having thus described the invention with reference to certain particular embodiments, it will be readily apparent to those skilled in the art that numerous modifications and substitutions can be made without departing from the scope and spirit of the invention.

We claim:

1. An apparatus for the treatment of wash water from the manufacture of terephthalic acid by a liquid-phase air oxidation of p-xylene, wherein the wash water contains terephthalic acid, metal catalysts and organic acid byproducts, said apparatus comprising:
   a first bed containing a strong acid cation exchange resin for removing said metal catalysts from said wash water;
   a second bed containing an anion exchange resin selected from the group consisting of weak base or intermediate base anion exchange resin for removing dissolved terephthalic acid and dissolved organic acid byproducts from said wash water;
   connecting conduits adapted first to pass wash water comprising dissolved terephthalic acid, metal catalysts and dissolved organic acid byproducts through said first bed, whereupon said metal catalysts are removed, and then to pass wash water comprising dissolved terephthalic acid and dissolved organic acid byproducts through said second bed, whereupon said acid and byproducts are removed;
   a supply of hydrobromic acid for regenerating said cation exchange resin after it has removed a quantity of said metal catalysts;
   a conduit for passing said supply of hydrobromic acid through said cation exchange resin;
   a supply of acetic acid for regenerating said anion exchange resin after it has removed a quantity of said dissolved terephthalic acid and dissolved organic acid byproducts; and
   a conduit for passing said supply of acetic acid through said anion exchange resin.

2. The apparatus of claim 1 further comprising a filter medium having a granule diameter of from about 0.3 to 1.0 mm for removing undissolved terephthalic acid solids and undissolved solids of organic acid byproducts from said wash water, wherein said connecting conduits are further adapted to pass wash water comprising said solids through said filter medium before being passed through said first bed, said filter medium removing said solids.

3. The apparatus of claim 2 further comprising a conduit adapted to pass water through said filter medium in a direction opposite to that in which said wash water passes through said filter medium, such that said solids removed by said filter medium are removed from said filter medium by said water moving in said opposite direction.

4. The apparatus of claim 1 further comprising a supply of an alkali selected from the group consisting of ammonia, sodium carbonate, potassium hydroxide and sodium hydroxide for regenerating said anion exchange resin by removing said acetic acid therefrom, and a conduit for passing said supply of alkali through said anion exchange resin.

5. An apparatus for the treatment of wash water from the manufacture of terephthalic acid by a liquid-phase air oxidation of p-xylene, wherein the wash water contains terephthalic acid, metal catalysts and organic acid byproducts, said apparatus comprising:
   a filter medium having a granule diameter of from about 0.3 to 1.0 mm for removing undissolved terephthalic acid solids and undissolved solids of organic acid byproducts from said wash water;
   a first bed containing a strong acid cation exchange resin for removing said metal catalysts from said wash water;
   a second bed containing an anion exchange resin selected from the group consisting of weak base or intermediate base anion exchange resin for removing dissolved terephthalic acid and dissolved orgainc acid byproducts from said wash water;
   connecting conduits for passing said wash water first through said filter medium, then through said first bed, and then through said second bed;
   a conduit adapted to pass water through said filter medium in a direction opposite to that in which said wash water passes through said filter medium, such that said solids removed by said filter medium are removed from said filter medium by said water moving in said opposite direction;
   a supply of hydrobromic acid for regenerating said cation exchange resin after it has removed a quantity of said metal catalysts;
   a conduit for passing said supply of hydrobromic acid through said cation exchange resin;
   a supply of acetic acid for regenerating said anion exchange resin after it has removed a quantity of said dissolved terephthalic acid and dissolved organic acid byproducts;
   a conduit for passing said supply of acetic acid through said anion exchange resin;
   a supply of an alkali selected from the group consisting of ammonia, sodium carbonate, potassium hydroxide and sodium hydroxide for regenerating said anion exchange resin by removing said acetic acid therefrom; and
   a conduit for passing said supply of alkali through said anion exchange resin.

* * * * *